US008337494B2

(12) United States Patent
Suslov

(10) Patent No.: US 8,337,494 B2
(45) Date of Patent: *Dec. 25, 2012

(54) PLASMA-GENERATING DEVICE HAVING A PLASMA CHAMBER

(75) Inventor: Nikolay Suslov, Atlanta, GA (US)

(73) Assignee: Plasma Surgical Investments Limited, Tortola (VG)

( * ) Notice: Subject to any disclaimer, the term of this patent is extended or adjusted under 35 U.S.C. 154(b) by 0 days.

This patent is subject to a terminal disclaimer.

(21) Appl. No.: 13/358,934

(22) Filed: Jan. 26, 2012

(65) Prior Publication Data

US 2012/0143184 A1 Jun. 7, 2012

Related U.S. Application Data

(63) Continuation of application No. 11/482,581, filed on Jul. 7, 2006, now Pat. No. 8,109,928.

(30) Foreign Application Priority Data

Jul. 8, 2005 (SE) .................................... 0501604-3

(51) Int. Cl.
*A61B 18/14* (2006.01)

(52) U.S. Cl. ........................................... 606/45; 606/39

(58) Field of Classification Search .................... 606/40, 606/45, 49; 315/111.21
See application file for complete search history.

(56) References Cited

U.S. PATENT DOCUMENTS

| | | | |
|---|---|---|---|
| 3,077,108 | A | 2/1963 | Gage et al. |
| 3,082,314 | A | 3/1963 | Yoshiaki et al. |
| 3,100,489 | A | 8/1963 | Bagley |
| 3,145,287 | A | 8/1964 | Seibein et al. |
| 3,153,133 | A | 10/1964 | Ducati |
| 3,270,745 | A | 9/1966 | Wood |
| 3,360,988 | A | 1/1968 | Stein et al. |
| 3,413,509 | A | 11/1968 | Cann et al. |
| 3,433,991 | A | 3/1969 | Whyman |
| 3,434,476 | A | 3/1969 | Shaw et al. |
| 3,534,388 | A | 10/1970 | Akiyama Osamu et al. |
| 3,628,079 | A | 12/1971 | Dobbs et al. |
| 3,676,638 | A | 7/1972 | Stand |
| 3,775,825 | A | 12/1973 | Wood et al. |

(Continued)

FOREIGN PATENT DOCUMENTS

| | | |
|---|---|---|
| AU | 2000250426 | 6/2005 |

(Continued)

OTHER PUBLICATIONS

Chinese Office Action of application No. 200780100857.9, dated Nov. 28, 2011 (with English translation).

(Continued)

*Primary Examiner* — Linda Dvorak
*Assistant Examiner* — Jaymi Della
(74) *Attorney, Agent, or Firm* — Jones Day

(57) ABSTRACT

A plasma-generating device comprising an anode, a plurality of intermediate electrodes, an insulator sleeve, and a cathode is disclosed. The plurality of the intermediate electrodes and the anode form a plasma channel. One of the intermediate electrodes forms a plasma chamber. The cathode has a tapering portion that projects downstream the distal end of the insulator sleeve only partially. Also, the distal-most point of the cathode is located some distance away from the plasma channel inlet. Methods of surgical use of the plasma-generating device are also disclosed.

28 Claims, 1 Drawing Sheet

U.S. PATENT DOCUMENTS

| | | | |
|---|---|---|---|
| 3,803,380 A | | 4/1974 | Ragaller |
| 3,838,242 A | | 9/1974 | Goucher |
| 3,851,140 A | | 11/1974 | Coucher |
| 3,866,089 A | | 2/1975 | Hengartner |
| 3,903,891 A | | 9/1975 | Brayshaw |
| 3,914,573 A | | 10/1975 | Muehlberger |
| 3,938,525 A | | 2/1976 | Coucher |
| 3,991,764 A | | 11/1976 | Incropera et al. |
| 3,995,138 A | | 11/1976 | Kalev et al. |
| 4,029,930 A | | 6/1977 | Sagara et al. |
| 4,035,684 A | | 7/1977 | Svoboda et al. |
| 4,041,952 A | | 8/1977 | Morrison, Jr. et al. |
| 4,201,314 A | | 5/1980 | Samuels et al. |
| 4,256,779 A | | 3/1981 | Sokol et al. |
| 4,317,984 A | | 3/1982 | Fridlyand |
| 4,397,312 A | | 8/1983 | Molko |
| 4,445,021 A | | 4/1984 | Irons et al. |
| 4,620,080 A | | 10/1986 | Arata et al. |
| 4,661,682 A | | 4/1987 | Gruner et al. |
| 4,672,163 A | | 6/1987 | Matsui et al. |
| 4,674,683 A | | 6/1987 | Fabel |
| 4,682,598 A | | 7/1987 | Beraha |
| 4,696,855 A | | 9/1987 | Pettit et al. |
| 4,711,627 A | | 12/1987 | Oeschsle et al. |
| 4,713,170 A | | 12/1987 | Saibic |
| 4,743,734 A | | 5/1988 | Garlanov et al. |
| 4,764,656 A | | 8/1988 | Browning |
| 4,777,949 A | | 10/1988 | Perlin |
| 4,780,591 A | | 10/1988 | Bernecki et al. |
| 4,781,175 A | | 11/1988 | McGreevy et al. |
| 4,784,321 A | | 11/1988 | Delaplace |
| 4,785,220 A | | 11/1988 | Brown et al. |
| 4,839,492 A | | 6/1989 | Bouchier et al. |
| 4,841,114 A | | 6/1989 | Browning |
| 4,853,515 A | | 8/1989 | Willen et al. |
| 4,855,563 A | | 8/1989 | Beresnev et al. |
| 4,866,240 A | | 9/1989 | Webber |
| 4,869,936 A | | 9/1989 | Moskowitz et al. |
| 4,874,988 A | | 10/1989 | English et al. |
| 4,877,937 A | | 10/1989 | Muller |
| 4,916,273 A | | 4/1990 | Browning |
| 4,924,059 A | | 5/1990 | Rotolico et al. |
| 5,008,511 A | | 4/1991 | Ross |
| 5,013,883 A | | 5/1991 | Fuimefreddo et al. |
| 5,100,402 A | | 3/1992 | Fan |
| 5,144,110 A | | 9/1992 | Marantz et al. |
| 5,151,102 A | | 9/1992 | Kamiyama et al. |
| 5,201,900 A | | 4/1993 | Nardella |
| 5,207,691 A | | 5/1993 | Nardella |
| 5,211,646 A | | 5/1993 | Alperovich et al. |
| 5,217,460 A | | 6/1993 | Knoepfler |
| 5,225,652 A | | 7/1993 | Landes |
| 5,227,603 A | | 7/1993 | Doolette et al. |
| 5,261,905 A | | 11/1993 | Doresey |
| 5,285,967 A | | 2/1994 | Weidman |
| 5,332,885 A | | 7/1994 | Landes |
| 5,352,219 A | | 10/1994 | Reddy |
| 5,396,882 A | | 3/1995 | Zapol |
| 5,403,312 A | | 4/1995 | Yates et al. |
| 5,406,046 A | | 4/1995 | Landes |
| 5,408,066 A | | 4/1995 | Trapani et al. |
| 5,412,173 A | | 5/1995 | Muehlberger |
| 5,445,638 A | | 8/1995 | Rydell et al. |
| 5,452,854 A | | 9/1995 | Keller |
| 5,460,629 A | | 10/1995 | Shlain et al. |
| 5,485,721 A | | 1/1996 | Steenborg |
| 5,514,848 A | | 5/1996 | Ross et al. |
| 5,519,183 A | | 5/1996 | Mueller |
| 5,527,313 A | | 6/1996 | Scott et al. |
| 5,573,682 A | | 11/1996 | Beason et al. |
| 5,582,611 A | | 12/1996 | Tsuruta et al. |
| 5,620,616 A | | 4/1997 | Anderson et al. |
| 5,629,585 A | | 5/1997 | Altmann |
| 5,637,242 A | | 6/1997 | Muehlberger |
| 5,640,843 A | | 6/1997 | Aston |
| 5,662,680 A | | 9/1997 | Desai |
| 5,665,085 A | | 9/1997 | Nardella |
| 5,679,167 A | | 10/1997 | Muehlberger |
| 5,680,014 A | | 10/1997 | Miyamoto et al. |
| 5,688,270 A | | 11/1997 | Yates et al. |
| 5,697,281 A | | 12/1997 | Eggers et al. |
| 5,697,882 A | | 12/1997 | Eggers et al. |
| 5,702,390 A | | 12/1997 | Austin et al. |
| 5,720,745 A | | 2/1998 | Farin et al. |
| 5,733,662 A | | 3/1998 | Bogachek |
| 5,797,941 A | | 8/1998 | Schulze et al. |
| 5,827,271 A | | 10/1998 | Buysse et al. |
| 5,833,690 A | | 11/1998 | Yates et al. |
| 5,837,959 A | | 11/1998 | Muehlberger et al. |
| 5,843,079 A | | 12/1998 | Suslov |
| 5,858,469 A | | 1/1999 | Sahoo et al. |
| 5,858,470 A | | 1/1999 | Bernecki et al. |
| 5,897,059 A | | 4/1999 | Muller |
| 5,906,757 A | | 5/1999 | Kong et al. |
| 5,932,293 A | | 8/1999 | Belashchenko et al. |
| 6,003,788 A | | 12/1999 | Sedov |
| 6,042,019 A | | 3/2000 | Rusch |
| 6,099,523 A | * | 8/2000 | Kim et al. ....................... 606/40 |
| 6,114,649 A | | 9/2000 | Delcea |
| 6,202,939 B1 | | 9/2000 | Delcea |
| 6,135,998 A | | 10/2000 | Palanker |
| 6,137,078 A | | 10/2000 | Keller |
| 6,162,220 A | | 12/2000 | Nezhat |
| 6,169,370 B1 | | 1/2001 | Platzer |
| 6,181,053 B1 | | 1/2001 | Roberts |
| 6,273,789 B1 | | 8/2001 | Lasalle et al. |
| 6,283,386 B1 | | 9/2001 | Van Steenkiste et al. |
| 6,322,856 B1 | | 11/2001 | Hislop |
| 6,352,533 B1 | | 3/2002 | Ellman et al. |
| 6,386,140 B1 | | 5/2002 | Muller et al. |
| 6,392,189 B1 | | 5/2002 | Delcea |
| 6,443,948 B1 | | 9/2002 | Suslov |
| 6,475,215 B1 | | 11/2002 | Tanrisever |
| 6,514,252 B2 | | 2/2003 | Nezhat et al. |
| 6,528,947 B1 | | 3/2003 | Chen et al. |
| 6,548,817 B1 | | 4/2003 | Anders |
| 6,562,037 B2 | | 5/2003 | Paton et al. |
| 6,629,974 B2 | | 10/2003 | Penny et al. |
| 6,634,571 B2 | | 10/2003 | Shimazu |
| 6,636,545 B2 | | 10/2003 | Krasnov |
| 6,657,152 B2 | | 12/2003 | Shimazu |
| 6,669,106 B2 | | 12/2003 | Delcea |
| 6,676,655 B2 | | 1/2004 | Mcdaniel |
| 6,730,343 B2 | | 5/2004 | Yossepowitch |
| 6,780,184 B2 | | 8/2004 | Tanrisever |
| 6,808,525 B2 | | 10/2004 | Latterell et al. |
| 6,811,812 B2 | | 11/2004 | Van Steenkiste |
| 6,844,560 B2 | | 1/2005 | Wieland et al. |
| 6,845,929 B2 | | 1/2005 | Dolatabadi et al. |
| 6,886,757 B2 | | 5/2005 | Byrnes et al. |
| 6,958,063 B1 | | 10/2005 | Soll et al. |
| 6,972,138 B2 | | 12/2005 | Heinrich et al. |
| 6,986,471 B1 | | 1/2006 | Kowalsky et al. |
| 7,025,764 B2 | | 4/2006 | Paton et al. |
| 7,030,336 B1 | | 4/2006 | Hawley |
| 7,118,570 B2 | | 10/2006 | Tetzlaff et al. |
| 7,132,619 B2 | | 11/2006 | Conway |
| 7,216,814 B2 | | 5/2007 | Gardega |
| 7,261,556 B2 | | 8/2007 | Belashchenko et al. |
| 7,276,065 B2 | | 10/2007 | Morley et al. |
| 7,291,804 B2 | | 11/2007 | Suslov |
| 7,316,682 B2 | | 1/2008 | Konesky |
| 7,361,175 B2 | | 4/2008 | Suslov |
| 7,431,721 B2 | | 10/2008 | Paton et al. |
| 7,540,873 B2 | | 6/2009 | Bayat |
| 7,557,324 B2 | | 7/2009 | Nylen et al. |
| 7,582,846 B2 | | 9/2009 | Molz et al. |
| 7,589,473 B2 | | 9/2009 | Suslov |
| 7,608,797 B2 | | 10/2009 | Belashchenko et al. |
| 7,621,930 B2 | | 11/2009 | Houser |
| 7,750,265 B2 | | 7/2010 | Belashchenko |
| 7,854,735 B2 | | 12/2010 | Houser et al. |
| 7,892,609 B2 | | 2/2011 | Muller |
| 7,928,338 B2 | | 4/2011 | Suslov |
| 7,955,328 B2 | | 6/2011 | Long et al. |
| 8,030,849 B2 | | 10/2011 | Suslov |
| 8,105,325 B2 | | 1/2012 | Suslov |

| | | | |
|---|---|---|---|
| 8,109,928 | B2 | 2/2012 | Suslov |
| 2002/0071906 | A1 | 6/2002 | Rusch |
| 2003/0125728 | A1 | 7/2003 | Nezhat et al. |
| 2004/0068304 | A1 | 4/2004 | Paton et al. |
| 2004/0124256 | A1 | 7/2004 | Itsukaichi et al. |
| 2005/0192610 | A1 | 9/2005 | Houser et al. |
| 2005/0192611 | A1 | 9/2005 | Houser |
| 2005/0192612 | A1 | 9/2005 | Houser et al. |
| 2006/0049149 | A1 | 3/2006 | Shimazu |
| 2006/0091117 | A1 | 5/2006 | Blankenship et al. |
| 2006/0091119 | A1 | 5/2006 | Zajchowski et al. |
| 2006/0189976 | A1 | 8/2006 | Karni et al. |
| 2006/0217706 | A1 | 9/2006 | Lau et al. |
| 2007/0029292 | A1 | 2/2007 | Suslov et al. |
| 2007/0173872 | A1 | 7/2007 | Neuenfeldt |
| 2008/0015566 | A1 | 1/2008 | Livneh |
| 2008/0071206 | A1 | 3/2008 | Peters |
| 2009/0039789 | A1 | 2/2009 | Nikolay |
| 2011/0190752 | A1 | 8/2011 | Suslov |
| 2012/0022522 | A1 | 1/2012 | Suslov |

FOREIGN PATENT DOCUMENTS

| | | | |
|---|---|---|---|
| AU | 2006252145 | | 1/2007 |
| CA | 983586 | | 2/1979 |
| CA | 1144104 | | 4/1983 |
| CA | 1308722 | | 10/1992 |
| CA | 2594515 | | 7/2006 |
| CN | 85107499 | B | 4/1987 |
| CN | 1331836 | | 1/2002 |
| CN | 1557731 | | 12/2004 |
| CN | 1682578 | A | 10/2005 |
| DE | 2033072 | | 2/1971 |
| DE | 10127261 | | 9/1993 |
| DE | 4209005 | | 12/2002 |
| EP | 0411170 | | 2/1991 |
| EP | 0748149 | | 12/1996 |
| EP | 0851040 | | 7/1998 |
| EP | 1293169 | | 3/2003 |
| EP | 1570798 | | 9/2005 |
| ES | 2026344 | | 4/1992 |
| FR | 2193299 | | 2/1974 |
| FR | 2567747 | | 1/1986 |
| GB | 751735 | | 7/1956 |
| GB | 921016 | | 3/1963 |
| GB | 1125806 | | 9/1968 |
| GB | 1176333 | | 1/1970 |
| GB | 1268843 | | 3/1972 |
| GB | 2407050 | | 4/2005 |
| JP | 47009252 | | 3/1972 |
| JP | 52-117255 | A | 10/1977 |
| JP | 54120545 | | 2/1979 |
| JP | 57001580 | | 1/1982 |
| JP | 57068269 | | 4/1982 |
| JP | 6113600 | | 1/1986 |
| JP | A-S61-193783 | | 8/1986 |
| JP | A-S61-286075 | | 12/1986 |
| JP | 62123004 | | 6/1987 |
| JP | 1198539 | | 8/1989 |
| JP | 1-319297 | A | 12/1989 |
| JP | 1319297 | | 12/1989 |
| JP | 3043678 | | 2/1991 |
| JP | 06262367 | | 9/1994 |
| JP | 9299380 | | 11/1997 |
| JP | 10024050 | | 1/1998 |
| JP | 10234744 | | 9/1998 |
| JP | 2002541902 | | 12/2002 |
| JP | 2008036001 | | 2/2008 |
| JP | 2008-284580 | A | 11/2008 |
| MX | PA04010281 | | 6/2005 |
| RU | 2178684 | | 1/2002 |
| RU | 2183480 | | 6/2002 |
| RU | 2183946 | | 6/2002 |
| WO | WO 92/19166 | | 11/1992 |
| WO | WO 96/06572 | | 3/1996 |
| WO | WO 97/11647 | | 4/1997 |
| WO | WO 01/62169 | | 8/2001 |
| WO | WO 02/30308 | | 4/2002 |
| WO | WO 03/28805 | | 4/2003 |
| WO | WO 2004/028221 | | 4/2004 |
| WO | WO 2004/030551 | | 4/2004 |
| WO | WO 2004/105450 | | 12/2004 |
| WO | WO 2005/099595 | | 10/2005 |
| WO | WO 2006/012165 | | 2/2006 |
| WO | WO 2007/003157 | | 1/2007 |
| WO | WO 2007/006516 | | 1/2007 |
| WO | WO 2007/006517 | | 1/2007 |
| WO | WO 2007/040702 | | 4/2007 |

OTHER PUBLICATIONS

U.S Appl. No. 13/357,895, filed Jan. 25, 2012, Suslov.

510(k) Notification (21 CFR 807.90(e)) for the Plasma Surgical Ltd. PlasmaJet® Neutral Plasma Surgery System, Section 10—Executive Summary—K080197.

510(k) Summary, dated Jun. 2, 2008.

510(k) Summary, dated Oct. 30, 2003.

Aptekman, 2007, "Spectroscopic analysis of the PlasmaJet argon plasma with 5mm-0.5 coag-cut handpieces", Document PSSRP-106—K080197.

Asawanonda et al., 2000, "308-nm excimer laser for the treatment of psoriasis: a dose-response study. "Arach. Dermatol. 136:619-24.

Branson, M.D., 2005, "Preliminary experience with neutral plasma, a new coagulation technology, in plastic surgery", Fayetteville, NY.

Charpentier et al., 2008, "Multicentric medical registry on the use of the Plasma. Surgical PlasmaJet System in thoracic surgery", Club Thorax.

Chen et al., 2006, "What do we know about long laminar plasma jets?", Pure Appl Chem; 78(6):1253-1264.

Cheng et al., 2006, "Comparison of laminar and turbulent thermal plasma jet characteristics—a modeling study", Plasma Chem Plasma Process; 26:211-235.

Chinese Office Action of application No. 200680030194.3, dated Jan. 31, 2011.

Chinese Office Action of application No. 200680030216.6, dated Oct. 26, 2010.

Chinese Office Action of application No. 200680030225.5, dated Jun. 11, 2010.

Chinese Office Action of application No. 200680030225.5, dated Mar. 9, 2011.

Chinese Office Action of application No. 2007801008583, dated Oct. 19, 2011 (with English translation).

CoagSafe™ Neutral Plasma Coagulator Operator Manual, Part No. OMC-2100-1, Revision 1.1, dated Mar. 2003—Appendix 1of K030819.

Coven et al., 1999, "PUVA-induced lymphocyte apoptosis: mechanism of action in psoriasis." Photodermatol. Photoimmunol. Photomed. 15:22-7.

Dabringhausen et al., 2002, "Determination of HID electrode falls in a model lamp I: Pyrometric measurements." J. Phys. D. Appl. Phys. 35:1621-1630.

Davis J.R. (ed) ASM Thermal Spray Society, Handbook of Thermal Spray Technology, 2004, U.S. 42-168.

Deb et al., "Histological quantification of the tissue damage caused in vivo by neutral PlasmaJet coagulator", Nottingham University Hospitals, Queen's medical Centre, Nottingham NG7 2UH—Poster.

Device drawings submitted pursuant to MPEP §724 in U.S. Appl. No. 11/482,581.

Electrosurgical Generators Force FX™ Electrosurgical Generators by ValleyLab—K080197.

ERBE APC 300 Argon Plasma Coagulation Unit for Endoscopic Applications, Brochure—Appendix 4 of K030819.

European Office Action of application No. 07786583.0/1226, dated Jun. 29, 2010.

Feldman et al., 2002, "Efficacy of the 308-nm excimer laser for treatment of psoriasis: results of a multicenter study." J. Am Acad. Dermatol. 46:900-6.

FORCE Argon™ II System, Improved precision and control in cicctrosurgcry, by Vallcylab—K080197.

Gerber et al., 2003, "Ultraviolet B 308-nm excimer laser treatment of psoriasis: a new phototherapeutic approach." Br. J. Dermatol. 149:1250-8.

Gugenheim et al., 2006, "Open, muliticentric, clinical evaluation of the technical efficacy, reliability, safety, and clinical tolerance of the plasma surgical PlasmaJet System for intra-operative coagulation in open and laparoscopic general surgery", Department of Digestive Surgery, University Hospital, Nice, France.
Haemmerich et al., 2003, "Hepatic radiofrequency ablation with internally cooled probes: effect of coolant temperature on lesion size", IEEE Transactions of Biomedical Engineering; 50(4):493-500.
Haines et al., "Argon neutral plasma energy for laparoscopy and open surgery recommended power settings and applications", Royal Surrey County Hospital, Guildford Surrey, UK.
Honigsmann, 2001, "Phototherapy for psoriasis." Clin. Exp. Dermatol. 26:343-50.
Huang et al., 2008, "Laminar/turbulent plasma jets generated at reduced pressure", IEEE Transaction on Plasma Science; 36(4):1052-1053.
Iannelli et al., 2005, "Neutral plasma coagulation (NPC)—A preliminary report on a new technique for post-bariatric correcteve abdominoplasty", Department of Digestive Surgery, University Hospital, Nice, France.
International Search Report of application No. PCT/EP2010/060641, dated Apr. 14, 2011.
International Preliminary Report on Patentability and Written Opinion of the International Searching Authority of International Application. PCT/EP2007/000919, dated Aug. 4, 2009.
International Preliminary Report on Patentability of International application No. PCT/EP2007/006939, dated Feb. 9, 2010.
International Preliminary Report on Patentability of International application No. PCT/EP2007/006940, dated Feb. 9, 2010.
International Search Report of International application No. PCT/EP2010/051130, dated Sep. 27, 2010.
International Search Report of International application PCT/EP2006/006690, dated Feb. 6, 2007.
International Search Report of International application PCT/EP2007/006939, dated May 26, 2008.
International Search Report of International application PCT/EP2007/006940, dated Jul. 11, 2008.
International-type Search report dated Jan. 18, 2006 of Swedish App. No. 0501603-5.
International-type Search report dated Jan. 18, 2006 of Swedish App. No. 0501602-7.
International-type Search report dated Jan. 18, 2006 of Swedish App. No. 0501604-3.
Japanese Office Action (translation) of application No. 2008-519873, dated Jun. 10, 2011.
Japanese Office Action (translation) of application No. 2009-547536, dated Feb. 15, 2012.
Letter to FDA re: 501(k) Notification (21 CFR 807.90(e)) for the PlasmaJet® Neutral Plasma Surgery System, dated Jun. 2, 2008—K080197.
Lichtenberg et al., 2002, "Observation of different modes of cathodic arc attachment to HID electrodes in a model lamp." J. Phys. D. Appl. Phys. 35:1648-1656.
Marino, M.D., "A new option for patients facing liver resection surgery", Thomas Jefferson University Hospital.
McClurken et al., "Collagen shrinkage and vessel sealing", TissueLink Medical, Inc., Dover, NH; Technical Brief #300.
McClurken et al., "Histologic characteristics of the TissueLink Floating Ball device coagulation on porcine liver", TissueLink Medical, Inc., Dover, NH; Pre-Clinical Study #204.
Merloz, 2007, "Clinical evaluation of the Plasma Surgical PlasmaJet tissue sealing system in orthopedic surgery—Early report", Orthopedic Surgery Department, University Hospital, Grenoble, France.
News Release and Video—2009, New Sugical Technology Offers Better Outcomes for Women's Reproductive Disorders: Stanford First in Bay Area to Offer PlasmaJet, Stanford Hospital and Clinics.
Nezhat et al., 2009, "Use of neutral argon plasma in the laparoscopic treatment of endometriosis", Journal of the Society of Laparoendoscopie Surgeons.
Notice of Allowance and Fees Due of U.S. Appl. No. 11/482,582, dated Sep. 23, 2011.
Notice of Allowance of U.S. Appl. No. 11/890,938, dated May 15, 2009.
Notice of Allowance of U.S. Appl. No. 12/557,645, dated May 26, 2011.
Notice of Allowance of U.S. Appl. No. 11/701,911, dated Dec. 6, 2010.
Office Action of U.S. Appl. No. 11/701,911, dated Apr. 17, 2008.
Office Action of U.S. Appl. No. 11/482,580, dated Feb. 1, 2008.
Office Action of U.S. Appl. No. 11/701,911, dated Mar. 13, 2009.
Office Action of U.S. Appl. No. 11/482,580, dated Mar. 19, 2009.
Office Action of U.S. Appl. No. 11/701,911, dated Oct. 18, 2007.
Office Action of U.S. Appl. No. 11/482,582, dated May 23, 2011.
Office Action of U.S. Appl. No. 11/482,583, dated Oct. 18, 2009.
Office Action of U.S. Appl. No. 11/701,911, dated Sep. 29, 2009.
Office Action of U.S. Appl. No. 11/890,937, dated Sep. 17, 2009.
Office Action of U.S. Appl. No. 11/482,582, dated Dec. 6, 2010.
Office Action of U.S. Appl. No. 11/482,582, dated Jun. 23, 2010.
Office Action of U.S. Appl. No. 11/701,911 dated Apr. 2, 2010.
Office Action of U.S. Appl. No. 11/701,911 dated Jul. 19, 2010.
Office Action of U.S. Appl. No. 11/890,937 dated Apr. 9, 2010.
Office Action of U.S. Appl. No. 12/557,645, dated Nov. 26, 2010.
Palanker et al., 2008, "Electrosurgery with cellular precision", IEEE Transactions of Biomedical Engineering; 55(2):838-841.
Pan et al., 2001, "Generation of long, laminar plasma jets at atmospheric pressure and effects of low turbulence", Plasma Chem Plasma Process; 21(1):23-35.
Pan et al., 2002, "Characteristics of argon laminar DC Plasma Jet at atmospheric pressure", Plasma Chem and Plasma Proc; 22(2):271-283.
PCT International Search Report International App. No. PCT/EP2006/006688, dated Feb. 14, 2007.
PCT International Search Report International App. No. PCT/EP2006/006689, dated Feb. 22, 2007.
PCT International Search Report International App. No. PCT/EP2007/000919, dated Oct. 23, 2007.
PCT Invitation to Pay Additional Fees PCT/EP2007/006940, dated May 20, 2008.
Written Opinion of International Application No. PCT/EP2007/000919, dated Oct. 23, 2007.
Written Opinion of International Application No. PCT/EP2006/006688, dated Feb. 14, 2007.
Written Opinion of International Application No. PCT/EP2006/006689, dated Feb. 22, 2007.
Written Opinion of International Application No. PCT/EP2006/006690, dated Feb. 22, 2007.
Plasma Surgery: A Patient Safety Solution (Study Guide 002).
Plasma Surgical Headlines Article: Atlanta, Feb. 2, 2010—"New Facilities Open in UK and US".
Plasma Surgical Headlines Article: Atlanta, Feb. 2, 2010—"PlasmaJet to be Featured in Live Case at Endometriosis 2010 in Milan, Italy".
Plasma Surgical Headlines Article: Chicago, Sep. 17, 2008—"PlasmaJet Named Innovation of the Year by the Society of Laparoendoscopic Surgeons".
PlasmaJet English Brochure.
PlasmaJet Neutral Plasma. Coagulator Brochure mpb 2100—K080197.
PlasmaJet Neutral Plasma Coagulator Operator Manual, Part No. OMC-2100-1 (Revision 1.7, dated May 2004)—K030819.
PlasmaJet Operator Manual Part No. OMC-2130-EN (Revision 3.1/Draft) dated May 2008—K080197.
Premarkct Notification 510(k) Submission, Plasma Surgical Ltd.—PlasmaJet™ (formerly CoagSafe™) Neutral Plasma Coagulator, Additional information provided in response to the e-mail request dated Jul. 14, 2004—K030819.
Premarket Notification 510(k) Submission, Plasma Surgical Ltd. CoagSafe™, Section 4 Device Description—K030819.
Premarket Notification 510(k) Submission, Plasma Surgical Ltd. CoagSafe™, Section 5 Substantial Equivalence—K030819.
Premarket Notification 510(k) Submission, Plasma Surgical Ltd. PlasmaJet®, Section 11 Device Description—K080197.
Report on the comparative analysis of morphological changes in tissue from different organs after using the PlasmaJet version 3 (including cutting handpieces), Aug. 2007—K080197.

Schmitz & Riemann, 2002, "Analysis of the cathode region of atmospheric pressure discharges." J. Phys. D. Appl. Phys. 35:1727-1735.
Severtsev et al. 1997, "Polycystic liver disease: sclerotherapy, surgery and sealing of cysts with fibrin sealant", European Congress of the International Hepatobiliary Association, Hamburg, Germany Jun. 8- 12; p. 259-263.
Severtsev et al., "Comparison of different equipment for final haemostasis of the wound surface of the liver following resection", Dept. of Surgery, Postgraduate and Research Centre, Medical Centre of the Directorate of Presidential Affairs of the Russian Federation, Moscow, Russia—K030819.
Sonoda et al., "Pathologic analysis of ex-vivo plasma energy tumor destruction in patients with ovarian or peritoneal cancer", Gynecology Service, Department of Surgery—Memorial Sloan-Kettering Cancer Center, New York, NY—Poster.
Supplemental Notice of Allowance of U.S. Appl. No. 11/482,582, dated Oct. 12, 2011.
The Edge in Electrosurgery From Birtcher, Brochure—Appendix 4 of K030819.
The Valleylab Force GSU System, Brochure—Appendix 4 of K030819.
Treat, "A new thermal device for sealing and dividing blood vessels", Dept. of Surgery, Columbia University, New York, NY.
Trehan & Taylor, 2002, "Medium-dose 308-nm excimer laser for the treatment of psoriasis." J. Am. Acad. Dermatol. 47:701-8.
Video—Laparoscopic Management of Pelvic Endometriosis, by Ceana Nezhat, M.D.
Video—Tissue Coagulation, by Denis F. Branson, M.D.
Video—Tumor Destruction Using Plasma Surgery, by Douglas A. Levine, M.D.
White Paper—A Tissue Study using the PlasmaJet for coagulation: A tissue study comparing the PlasmaJet with argon enhanced electrosurgery and fluid coupled electrosurgery.
White Paper—Plasma Technology and its Clinical Application: An introduction to Plasma Surgery and the PlasmaJet—a new surgical technology.
Written Opinion of International application No. PCT/EP2010/051130, dated Sep. 27, 2010.
Written Opinion of International application PCT/EP2007/006939, dated May 26, 2008.
Written Opinion of International application No. PCT/EP2010/060641, dated Apr. 14, 2011.
Written Opinion of International application PCT/EP2007/006940, dated Jul. 11, 2008.
www.plasmasurgical.com, as of Feb. 18, 2010.
Zenker, 2008, "Argon plasma coagulation", German Medical Science; 3(1):1-5.
Chinese Office Action of application No. 200780052471.5, dated May 25, 2012 (with English translation).
Chinese Office Action of application No. 200780100857.9, dated May 25, 2012 (with English translation).
Office Action of U.S. Appl. No. 13/357,895, dated Mar. 29, 2012.
Office Action of U.S. Appl. No. 11/482,580, dated Apr. 11, 2012.
Japanese Office Action of application No. 2010-519340, dated Mar. 13, 2012 (with translation).
Chinese Office Action of application No. 200780100858.3, dated Apr. 27, 2012 (with English translation).
Japanese Office Action of application No. 2010-519339, dated Apr. 3, 2012 (with English translation).
Office Action of U.S. Appl. No. 13/357,895, dated Sep. 7, 2012.
Chinese Office Action of Chinese application No. 200780100858.3, dated Aug. 29, 2012.
Office Action of U.S. Appl. No. 11/482,580, dated Oct. 24, 2012.

* cited by examiner

PLASMA-GENERATING DEVICE HAVING A PLASMA CHAMBER

CLAIM OF PRIORITY

This application is a continuation of U.S. application Ser. 11/482,581 filed on Jul. 7, 2006, now U.S. Pat. No. 8,109,928 which claims priority of a Swedish Patent Application No. 0501604-3 filed on Jul. 8, 2005.

FIELD OF THE INVENTION

The present invention relates to a plasma-generating device, comprising an anode, a cathode and a plasma channel which in its longitudinal direction extends at least partly from a point located between the cathode and the anode, and through the anode. The invention also relates to a plasma surgical device and the use of the plasma surgical device in the field of surgery.

BACKGROUND ART

Plasma devices refer to devices configured for generating plasma. Such plasma can be used, for example, in surgery for destruction (dissection, vaporization) and/or coagulation of biological tissues.

As a general rule, such plasma devices have a long and narrow end that can be easily held and pointed toward a desired area to be treated, such as bleeding tissue. Plasma is discharged at a distal portion of the device. The high temperature of plasma allows for treatment of the affected tissue.

WO 2004/030551 (Suslov) discloses a plasma surgical device according to prior art. This device comprises an anode, a cathode, and a gas supply channel for supplying plasma-generating gas from the plasma-generating system. The device further comprises a number of electrodes arranged upstream of the anode. A housing of an electrically conductive material which is connected to the anode encloses the device and forms the gas supply channel.

Owing to the recent developments in surgical technology, laparoscopic (keyhole) surgery is being used more often. Performing laparoscopic surgery requires devices with small dimensions to allow access to the surgical site without extensive incisions. Small instruments are also advantageous in any surgical operation for achieving good accuracy.

When making plasma devices with small dimensions, there is often a risk that due to the temperature of the cathode, which in some cases may exceed 3000° C., other elements in the proximity of the cathode would be heated to high temperatures. At these temperatures, there is a risk that these elements may be degraded, thus, contaminating the generated plasma. Contaminated plasma may introduce undesirable particles into the surgical area, which may be harmful to a patient.

Thus, there is a need for improved plasma devices, in particular plasma devices with small dimensions that can produce high temperature plasma.

SUMMARY OF THE INVENTION

An object of the present invention is to provide an improved plasma-generating device. Plasma is generated inside the device and is discharged from the discharge end, also referred to as the distal end. In general, the term "distal" refers to facing the discharge end of the device; the term "proximal" refers to facing the opposite direction. The terms "distal" and "proximal" can be used to describe the ends of the device and its elements.

Additional objects of the invention are to provide a plasma surgical device and a method of use of such a plasma surgical device in the field of surgery.

According to one aspect of the invention, a plasma-generating device comprising an anode, a cathode and a plasma channel that in its longitudinal direction extends at least partly between the cathode and the anode is provided. The plasma channel has an inlet located between the distal end of the cathode and the anode; the plasma channel has an outlet located at the distal end of the device. According to the invention, the cathode's distal portion has a tip tapering toward the anode, a part of the cathode tip extending over a partial length of a plasma chamber connected to the inlet of the plasma channel. (In the remainder of the disclosure, unless expressly stated otherwise, the term "cross-section" and its variations refer to a cross-section transverse to the longitudinal axis of the device.) The plasma chamber has a cross-sectional area that is greater than a cross-sectional area of the plasma channel at its inlet.

The plasma channel is an elongate channel in fluid communication with the plasma chamber. In one embodiment, the plasma channel extends from the plasma chamber toward and through the anode. The plasma channel has an outlet in the anode. In operation, the generated plasma is discharged through this outlet. The plasma chamber has a cylindrical portion and, preferably, a transitional portion between the plasma channel and the cylindrical portion of the plasma chamber. Alternatively, the cylindrical portion of the plasma chamber and the plasma channel can be in direct contact with each other.

The plasma chamber is the space in which a plasma-generating gas, supplied to the plasma-generating device, is mainly converted to plasma. With a device according to the invention, completely new conditions of generating such a plasma are provided.

In prior art plasma-generating devices, damage and degeneration of the elements surrounding the cathode, due to its high temperature, were prevented by placing these elements at considerable distances from the cathode. On the other hand, in the prior art, the tip of the cathode was often placed at the inlet of the plasma channel to ensure that the electric arc terminates in the plasma channel. Due to high temperatures of the cathode, distances between the cathode and other elements had to be made large, which resulted in considerably large dimensions of the device relative to the dimensions of the cathode. Such prior art devices thus had diameters greater than 10 mm, which can be unwieldy and difficult to handle. In addition such devices were unfit for laparoscopic (keyhole) surgery and other space-limited applications.

By having a plasma chamber, a portion of which is between the cathode distal end and the plasma channel inlet, it is possible to provide a plasma-generating device with smaller outer dimensions than those in the prior art.

For plasma-generating devices, it is not uncommon for the cathode tip to reach the temperature that exceeds 2,500° C., and in some cases 3,000° C., in operation.

The plasma chamber is a space around the cathode, especially the tip of the cathode. Consequently, the plasma chamber allows the outer dimensions of the plasma-generating device to be relatively small. The space around the cathode tip reduces the risk that, in operation, the high temperature of the cathode would damage and/or degrade other elements of the device in the proximity of the cathode tip. In particular, this is important for devices intended for surgical applications, where there is a risk that degraded material can contaminate the plasma and accompany the plasma into a surgical area, which may harm the patient. The plasma chamber is particularly advantageous for long continuous periods of operation.

A further advantage of having the plasma chamber is that an electric arc, which is intended to be generated between the cathode and the anode, can be reliably obtained since the plasma chamber allows the tip of the cathode to be positioned in the vicinity of the plasma channel inlet without contact with other elements, thus significantly reducing the risk of these elements being damaged and/or degraded due to the high temperature of the cathode. If the tip of the cathode is positioned at too great a distance from the inlet of the plasma channel, the electric spark between the cathode and the closest surface may be generated. This would result in the arc not entering the plasma channel, thus causing incorrect operation of the device and, in some cases, also damage to the device.

Embodiments of the invention can be particularly useful for miniaturized plasma-generating devices having a relatively small outer diameter, such as less than 10 mm, or even less than 5 mm. Plasma-generating devices embodying the invention can generate plasma with a temperature higher than 10,000° C. as the plasma is being discharged through the outlet of the plasma channel at the distal end of the device. For example, the plasma discharged through the outlet of the plasma channel can have a temperature between 10,000 and 15,000° C. Such high temperatures are possible as a result of making the cross-section of the plasma channel smaller. A smaller cross-section plasma channel, in turn, is possible because the distal end of the cathode does not have to be located in the plasma channel inlet and can be located some distance away from the inlet. A smaller cross-section of the plasma channel also improve accuracy of the plasma-generating device, compared with prior art devices.

It has also been found that properties of the plasma-generating device depend on the shape of the cathode tip and its position relative to an insulator sleeve arranged along and around the cathode. For example, it has been found that such an insulator sleeve is often damaged if it surrounds the entire cathode tip, due to a high temperature of the cathode tip in operation. It has also been found that in operation, a spark may occur between the cathode and the insulator sleeve if the entire cathode tip is positioned outside the insulator sleeve, in which case such a spark can damage the insulator sleeve and result in impurities.

In one embodiment, the insulator sleeve extends along and around parts of the cathode such that a partial length of the cathode tip projects beyond the distal boundary of the insulator sleeve. Preferably, the distal boundary of the insulator sleeve is a surface facing the anode. In operation, the insulator sleeve protects parts of the plasma-generating device arranged in the vicinity of the cathode from the cathode's high temperature in operation. The insulator sleeve may have different shapes, but it is preferably an elongated tube.

For proper operation of the plasma-generating device, it is essential that a spark generated at the cathode tip reaches a point in the plasma channel. This is accomplished by positioning the cathode so that the distance between (i) the distal end of the cathode and (ii) the proximal end of the plasma channel is less than or equal to the distance between (a) the distal end of the cathode and (b) any other surface. Specifically, the distal end of the cathode is closer to the inlet of the plasma channel than to any other point on the surface of the plasma chamber or of the insulator sleeve.

By arranging the cathode so that the tapering tip partially projects beyond the boundary surface of the insulator sleeve, a radial distance is established between the cathode tip and the boundary surface of the insulator sleeve. This distance minimizes the possibility that, in operation, the insulator sleeve would be damaged by the heat emanating from the cathode tip. The tapered shape of the cathode tip, used in the preferred embodiment, results in the progressive increase of the radial distance between the insulator sleeve and the cathode in the direction of the operational temperature increase (downstream). An advantage achieved by such a configuration is that a cross-sectional gap between the cathode and the insulator sleeve can be increased without increasing the outside dimensions of the device. Consequently, the outer dimensions of the plasma-generating device can be made suitable for laparoscopic surgery and other space-limited applications.

In the preferred embodiment, substantially half of the length of the cathode tip projects beyond the distal boundary surface of the insulator sleeve. This arrangement has been found particularly advantageous for reducing the possibility of insulator sleeve damage and the occurrence of the electric spark between the cathode and the insulator sleeve, as explained next.

During operation, a spark may be generated from an edge of the cathode at the base of the cathode tip as well as the distal-most point of the cathode tip. To prevent spark generation from the base of the cathode tip, the cathode is preferably positioned in a way that the distal-most point is closer to the plasma channel inlet than the edge at the base of the cathode tip to the boundary surface of the insulator sleeve.

In the preferred embodiment, the cathode tip projects beyond the boundary surface of the insulator sleeve by a length substantially corresponding to a diameter of the base of the cathode tip.

The length of the cathode tip refers to the length of the distal cathode end part, which tapers toward the anode. The tapering cathode tip connects to a proximal portion of the cathode with a substantially uniform diameter. In some embodiments, the tapering cathode tip is a cone. In some embodiments the cone may be truncated. Moreover, the base of the cathode tip is defined as a cross-section of the cathode area at a location where the tapering portion meets the portion with a substantially uniform diameter.

In operation, a plasma-generating gas flows in the gap formed by the inner surface of the insulator sleeve and the outside surface of the cathode.

In one embodiment, in the cross-section through a plane along the base of the cathode tip, the area of the gap formed by the insulator sleeve and the cathode is equal to or greater than a minimum cross-sectional area of the plasma channel. The minimum cross-sectional area of the plasma channel can be located anywhere along the plasma channel. This relationship ensures that the gap formed by the cathode and the insulator sleeve is not a "bottleneck" during the plasma-generating device startup. This facilitates a relatively quick buildup to the operating pressure of the plasma-generating device, which, in turn, results in shorter startup times. Short startup times are particularly convenient in cases when the operator starts and stops the operation of the plasma-generating device several times during a procedure. In one embodiment, the cross-sectional area of the insulator sleeve's hole is between 1.5 and 2.5 times the cross-sectional area of the cathode in a common cross-sectional plane.

In one embodiment, the insulator sleeve has an inner diameter in the range of 0.35 mm and 0.80 mm, preferably 0.50-0.60 mm, in the vicinity of the base of the cathode tip. It is appreciated, however, that the inner diameter of the insulator sleeve is greater than the diameter of the cathode in a common cross-section, thus forming a gap between them.

The cathode tip has a length that is greater than the diameter of the base of the cathode tip. In one embodiment, the length is equal to or greater than 1.5 times the diameter of the base of the cathode tip. The shape and the position of the tip relative to the insulator sleeve provides the distance between the cathode tip and the insulator sleeve (especially the insulator sleeve's distal surface). This distance prevents damage to the insulator element during operation of the plasma-generating device. In an alternative embodiment, the length of the cathode tip is 2-3 times the diameter of the base of the cathode tip.

As mentioned above, in the preferred embodiment the insulator sleeve extends along and around a portion of the cathode. The plasma chamber extends between a boundary surface of the insulator sleeve and the plasma channel inlet. Thus, the portion of the plasma chamber where the plasma-generating gas is mainly converted into plasma extends from the distal-most point of the cathode tip to the plasma channel inlet.

In one embodiment, the plasma chamber has a portion tapering toward the anode, which portion connects to the plasma channel. This tapering portion provides a transition between the cylindrical portion of the plasma chamber and the plasma channel inlet. This transitional portion facilitates favorable heat extraction for cooling of structures adjacent to the plasma chamber and the plasma channel.

It has been found optimal to make the cross-sectional area of the plasma chamber cylindrical portion about 4-16 times greater than a cross-sectional area of the plasma channel, preferably at the inlet. This relationship between the cross-sectional area of the plasma chamber cylindrical portion and of the plasma channel results in a space around the cathode tip. This space reduces the risk of damage to the plasma-generating device due to high temperatures which the cathode tip might reach in operation.

Preferably, the cross-section of the plasma chamber is circular. Preferably the plasma chamber diameter is approximately equal to the length of the plasma chamber. This relationship between the diameter and length of the plasma chamber has been found optimal for reducing the risk of thermal damage to the device elements, while at the same time reducing the possibility of the generation of a misdirected spark.

Preferably, the diameter of a cross-section of the cylindrical portion of the plasma chamber is 2-2.5 times a diameter of the cathode tip base.

Preferably, the length of the plasma chamber is 2-2.5 times the diameter of the base of the cathode tip.

It has been experimentally found that the functionality and operation of the plasma-generating device was affected by varying the position of the cathode tip with respect to the plasma channel inlet. Specifically, the generation of the electric arc was affected. For example, it has been observed that if the distal end of the cathode is positioned too far from the plasma channel inlet, an electric arc would be generated in an unfavorable manner between the cathode and another surface, but not in the plasma channel. Moreover, it has been found that if the cathode tip is positioned too close to the inlet of the plasma channel, there is a risk that, in operation, the cathode may touch an intermediate electrode. This will cause that electrode to heat up resulting in damage and degradation. In one embodiment, the cathode tip extends into the plasma chamber by half, or more than half, the length of the plasma chamber. In another embodiment, the cathode tip extends over ½ to ⅔ of the plasma chamber length.

In one embodiment, the distance between the distal end of the cathode and the inlet of the plasma channel is approximately equal to the length of the portion of the cathode tip that projects into the plasma chamber beyond the boundary surface of the insulator element.

Moreover, preferably, the distance between the distal end of the cathode and the plasma channel inlet is substantially equal to a diameter of the cathode tip base.

Positioning the distal-most point of the cathode tip at a distance from the inlet of the plasma channel ensures that an electric arc can be safely generated while at the same time reducing the risk that material of the elements forming the plasma channel are damaged by the heat emanating from the cathode in operation.

The plasma chamber is preferably formed by an intermediate electrode that shares a cross-section with the cathode tip. Because an intermediate electrode forms the plasma chamber, the structure of the device is relatively simple. Preferably, the plasma channel is formed at least partly by at least one intermediate electrode.

In one embodiment, the plasma chamber and at least a part of the plasma channel are formed by the intermediate electrode that shares a cross-section with the cathode tip. In another embodiment the plasma chamber is formed by an intermediate electrode that is electrically insulated from the intermediate electrodes forming the plasma channel.

In an exemplary embodiment of the plasma-generating device, the plasma channel has a diameter of about 0.20 to 0.50 mm, preferably 0.30-0.40 mm.

In one embodiment, the plasma-generating device comprises two or more intermediate electrodes forming at least a part of the plasma channel. In an exemplary embodiment, the intermediate electrodes jointly form a part of the plasma channel with a length of about 4 to 10 times a diameter of the plasma channel. The part of the plasma channel formed by the anode preferably has a length of 3-4 times the diameter of the plasma channel. Moreover, an insulator washer is arranged between each adjacent pair of intermediate electrodes as well as between the most-distal intermediate electrode and the anode. The intermediate electrodes are preferably made of copper or alloys containing copper.

In one embodiment, the diameter of the cathode at the base of the tip is between 0.30 and 0.60 mm, preferably 0.40 to 0.50 mm.

According to another aspect of the invention, a plasma surgical device comprising a plasma-generating device as described above is provided. Such a plasma surgical device may be used for destruction or coagulation of biological tissue. Moreover, such a plasma surgical device can be used in heart or brain surgery. In addition, such a plasma surgical device can be used in liver, spleen, or kidney surgery.

BRIEF DESCRIPTION OF THE DRAWING

The invention will now be described in more detail with reference to the accompanying schematic drawings, which, by way of example, illustrate preferred embodiments of the invention.

DESCRIPTION OF PREFERRED EMBODIMENTS

Figure 1A:
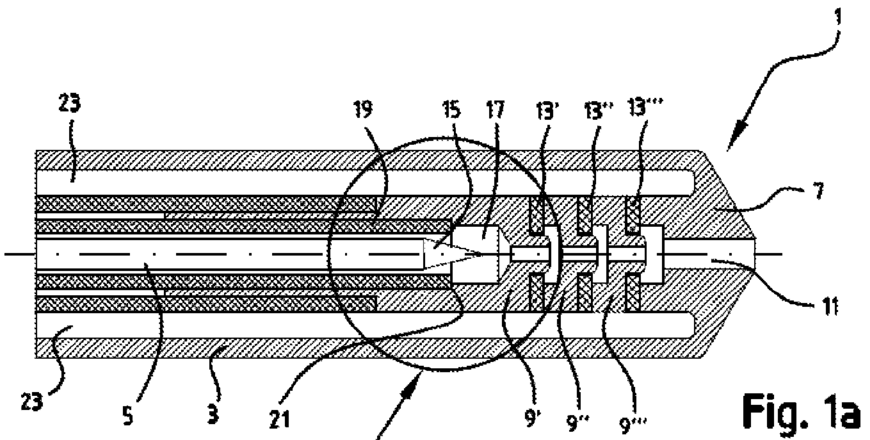
FIG. 1*a* is a longitudinal cross-sectional view of an embodiment of a plasma-generating device according to the invention.

FIG. 1*a* shows a longitudinal cross-section of one embodiment of a plasma-generating device 1 according to the invention. The cross-section in FIG. 1*a* is taken through the centre of the plasma-generating device 1 in its longitudinal direction. The device comprises an elongated end sleeve 3 that encloses other elements of the device. In operation, plasma flows from the proximal end of the device (left side of FIG. 1*a*) and is discharged at the end of the end sleeve 3 (right side of FIG. 1*a*). The flow of plasma gives meaning to the terms "upstream" and "downstream." The discharge end of sleeve 3 is also referred to as the distal end of device 1. In general, the term "distal" refers to facing the discharge end of the device; the term "proximal" refers to facing the opposite direction. The terms "distal" and "proximal" can be used to describe the ends of device 1 as well as its elements. The generated plasma can be used, for example, to stop bleeding in tissues, vaporize tissues, cut tissues, etc.

The plasma-generating device 1 according to FIG. 1*a* comprises cathode 5, anode 7, and a number of electrodes 9', 9'', 9''', referred to as intermediate electrodes in this disclosure, arranged upstream of anode 7. In the preferred embodiment, the intermediate electrodes 9', 9'', 9''' are annular and form a part of a plasma channel 11, which extends from a position downstream of cathode 5 and further toward and through anode 7. Inlet 35 (in FIG. 1*b*) of plasma channel 11 is at the proximal end the plasma channel. Plasma channel 11 extends through anode 7 where its outlet is arranged. In plasma channel 11, plasma is heated and discharged through the outlet. Intermediate electrodes 9', 9'', 9''' are insulated and separated from direct contact with each other by annular insulator washers 13', 13'', 13'''. The shape of the intermediate electrodes 9', 9'', and 9''' and the dimensions of the plasma channel 11 can be adjusted for any desired purpose. The number of intermediate electrodes 9', 9'', 9''' can also be varied. The exemplary embodiment shown in FIG. la is configured with three intermediate electrodes 9', 9'', 9'''.

In the embodiment shown in FIG. 1*a*, cathode 5 is formed as an elongate cylindrical element. Preferably, cathode 5 is made of tungsten, optionally with additives, such as lanthanum. Such additives can be used, for example, to lower the temperature that the distal end of cathode 5 reaches.

In the preferred embodiment, the distal portion of cathode 5 has a tapering end portion 15. Tapering portion 15 forms a tip, as shown in FIG. 1*a*. Preferably, cathode tip 15 is a cone. In some embodiments, cathode tip 15 is a truncated cone. In other embodiments, cathode tip 15 may have other shapes, tapering toward anode 7.

The proximal end of cathode 5 is connected to an electrical conductor to be connected to an electric energy source. The conductor, which is not shown in FIG. 1*a*, is preferably surrounded by an insulator.

Plasma chamber 17 is connected to the inlet of plasma channel 11. Plasma chamber 17 has cylindrical portion 32, and in the preferred embodiment also transitional portion 25. A cross-sectional area of cylindrical portion 32 is greater than a cross-sectional area of plasma channel inlet 35.

Plasma chamber 17, as shown in FIG. 1*a*, has circular cross-sections. In the preferred embodiment, the length of plasma chamber is approximately equal to the diameter of cylindrical portion 32. Plasma chamber 17 and plasma channel 11 are arranged substantially concentrically to each other. In the preferred embodiment, cathode 5 is arranged substantially concentrically with plasma chamber 17. Cathode 5 extends into plasma chamber 17 over approximately half of the plasma chamber 17's length. Plasma chamber 17 is formed by a recess in the most proximal intermediate electrode 9'.

FIG. 1*a* also shows insulator sleeve 19 extending along and around a portion of cathode 5. Cathode 5 is arranged substantially in the center of the through hole of insulator sleeve 19. The inner diameter of insulator sleeve 19 is slightly greater than the outer diameter of cathode 5. The difference in these diameters results in a gap formed by the outer surface of cathode 5 and the inner surface of insulator sleeve 19.

Preferably, insulator sleeve 19 is made of a temperature-resistant material, such as ceramic, temperature-resistant plastic, or the like. Insulator sleeve 19 protects constituent elements of plasma-generating device 1 from heat generated by cathode 5, and in particular by cathode tip 15, during operation.

Insulator sleeve 19 and cathode 5 are arranged relative to each other so that the distal end of cathode 5 projects beyond the distal end of insulator sleeve 19. In the embodiment shown in FIG. 1*a*, approximately half of the length of the cathode tip 15 extends beyond distal end of insulator sleeve 19, which, in that embodiment, is surface 21.

A gas supply part (not shown in FIG. 1) is connected to the plasma-generating device. The gas supplied, under pressure, to the plasma-generating device 1 consists of the same type of gases that are used in prior art instruments, for example, inert gases, such as argon, neon, xenon, or helium. The plasma-generating gas flows through the gas supply part and into the gap formed by the outside surface of cathode 5 and the inside surface of insulator sleeve 19. The plasma-generating gas flows along cathode 5 inside insulator sleeve 19 toward anode 7. (As mentioned above, this direction of the plasma flow gives meaning to the terms "upstream" and "downstream" as used herein.) As the plasma-generating gas passes distal end 21 of insulator sleeve 19, the gas enters into plasma chamber 17.

The plasma-generating device 1, shown in FIG. 1*a*, further has auxiliary channels 23. Auxiliary channels 23 traverse a substantial length of device 1. In some embodiments, a proximal portion of each channel 23 is formed, in part, by a housing (not shown) which is connected to end sleeve 3, while a distal end of each channel 23 is formed, in part, by end sleeve 3. End sleeve 3 and the housing can be interconnected by a threaded joint or by other coupling methods, such as welding, soldering, etc. Additional channels 23 can be made by extrusion of the housing or mechanical working of the housing. In alternative embodiments, auxiliary channels 23 can also be formed by one or more parts which are separate from the housing and arranged inside the housing.

In one embodiment, the plasma-generating device 1 has two auxiliary channels 23 connecting inside end sleeve 3 in the vicinity of anode 7. In this configuration, the auxillary channels collectively form a cooling system where one auxiliary channel 23 has an inlet and the other channel 23 has an outlet for a coolant in the proximal end of device 1. The two channels are connected with each other to allow the coolant to pass between them inside end sleeve 3. It is also possible to arrange more than two auxiliary channels in the plasma-generating device 1. Preferably, water is used as coolant, although other fluids are contemplated. The cooling channels are arranged so that the coolant is supplied to end sleeve 3 and flows between intermediate electrodes 9', 9'', 9''' and the inner wall of end sleeve 3.

Intermediate electrodes 9', 9'', 9''' and insulator washers 13', 13'', and 13''' are arranged inside end sleeve 3 of the plasma-generating device 1 and are positioned substantially concentrically with end sleeve 3. The intermediate electrodes 9', 9'', 9''' and insulator washers 13', 13'', and 13''' have outer surfaces, which together with the inner surface of sleeve 3 form auxiliary channels 23.

The number and cross-section of auxiliary channels 23 can vary. It is also possible to use all, or some, of auxiliary channels 23 for other purposes. For example, three auxiliary channels 23 can be arranged, with two of them being used for cooling, as described above, and the third one being used for removing undesired liquids or debris from the surgical site.

In the embodiment shown in FIG. 1*a*, three intermediate electrodes 9', 9'', 9''' are spaced apart by insulator washers 13', 13'', 13''' arranged between each pair of the intermediate electrodes, and between the distal-most intermediate electrode and anode 7. The first intermediate electrode 9', the first insulator 13'' and the second intermediate electrode 9'' are press-fitted to each other. Similarly, the second intermediate electrode 9'', the second insulator 13'' and the third intermediate electrode 9''' are press-fitted to each other. The number of intermediate electrodes 9', 9'', 9''' is not limited to three and can vary for different embodiments.

The proximal-most electrode 9''' is in contact with annular insulator washer 13''', which in turn is arranged against anode 7. While in the preferred embodiment, insulators 13 are washers, in other embodiments they can have any annular shape.

Anode 7 is connected to elongate end sleeve 3. In the embodiment shown in FIG. 1*a*, anode 7 and end sleeve 3 are formed integrally with each other. Note that in this configuration, "anode" refers to the portion of the joint structure that has a substantial positive charge. In alternative embodiments, anode 7 can be formed as a separate element which is coupled to end sleeve 3 by any known means, such as a threaded joint, welding, or soldering. The connection between anode 7 and end sleeve 3 provides electrical contact between them.

Figure 1B:
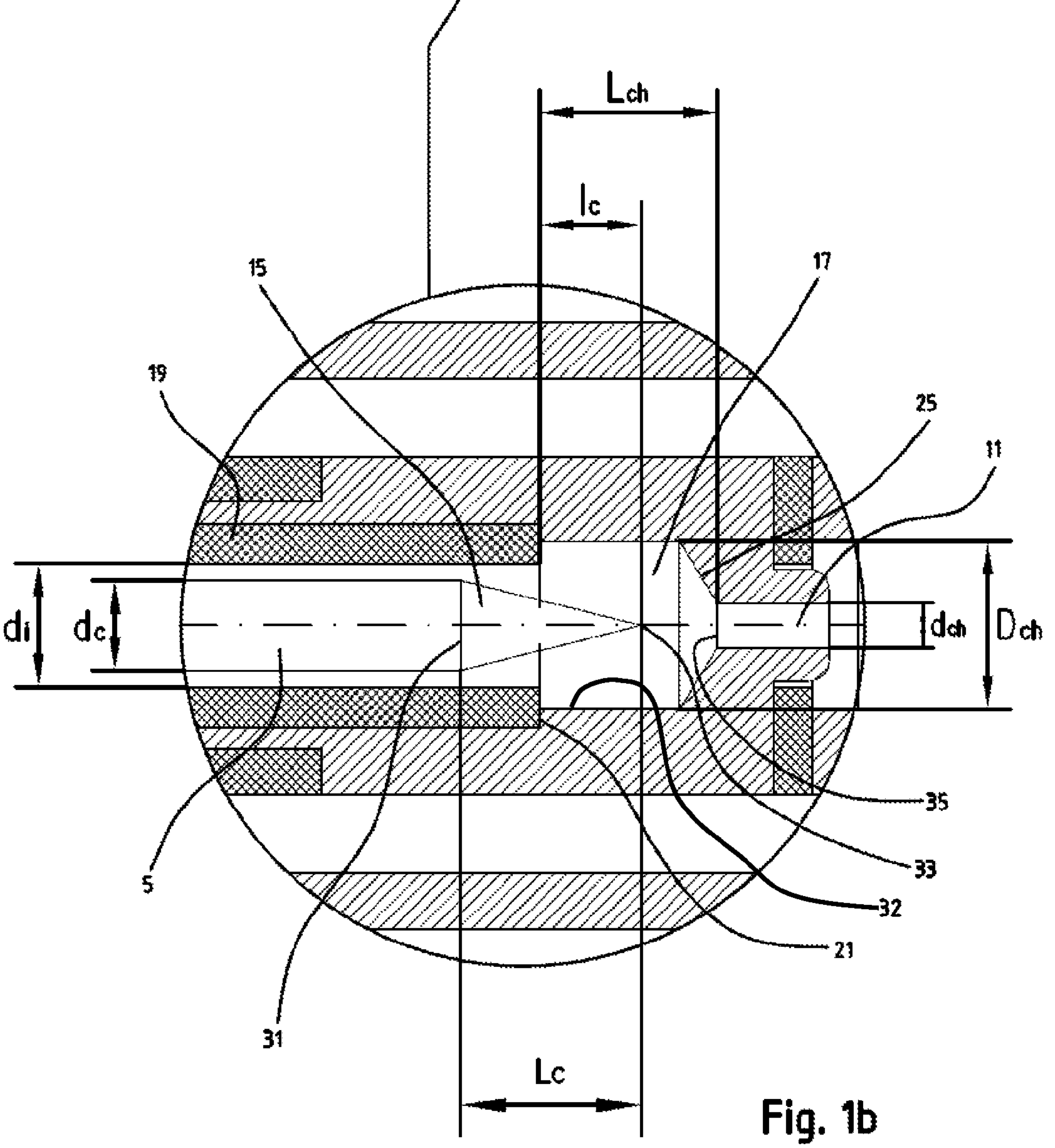
FIG. 1*b* is a partial enlargement of the embodiment according to FIG. 1*a*.

With reference to FIG. 1*b*, geometric relationships between the parts included in the plasma-generating device 1 are described below. It will be noted that the dimensions stated below merely constitute exemplary embodiments of the plasma-generating device 1 and can be varied according to the field of application and the desired plasma properties.

The inner diameter $d_i$ of insulator sleeve 19 is only slightly greater than the outer diameter $d_c$ of cathode 5. In the embodiment shown in FIG. 1*b*, the outer diameter $d_c$ of cathode 5 is about 0.50 mm and the inner diameter $d_i$ of insulator sleeve 19 is about 0.80 mm.

In FIG. 1*b*, tip 15 of cathode 5 is positioned so that about half the length of tip 15, $L_c$, projects beyond boundary surface 21 of insulator sleeve 19. In the depicted embodiment shown in FIG. 1*b*, this length of projection $l_c$ approximately equals diameter $d_c$ of cathode 5 at base 31 of tip 15.

The total length $L_c$ of cathode tip 15 is about 1.5-3 times diameter $d_c$ of cathode 5 at base 31 of cathode tip 15. In the embodiment shown in FIG. 1*b*, the length $L_c$ of cathode tip 15 is about 2 times the diameter $d_c$ of cathode 5 at base 31 of the cathode tip 15. In one embodiment, cathode 5 is positioned so that the distance between the distal-most point 33 of cathode tip 15 and the plasma channel inlet 35 is less than or equal to the distance between distal end 33 of cathode tip 15 and any other surface, including any surface of plasma chamber 17 and boundary surface 21 of insulator sleeve 19. Furthermore, in one embodiment, cathode 5 is positioned so that the distance between the distal end 33 of cathode tip 15 and the plasma channel inlet 35 is less than or equal to the distance between the edge at base 31 of cathode tip 15 and boundary surface 21 of insulator sleeve 19.

In one embodiment, the diameter $d_c$ of cathode 5 at base 31 of cathode tip 15 is approximately 0.3-0.6 mm. In the embodiment shown in FIG. 1*b*, the diameter $d_c$ of cathode 5 at base 31 of tip 15 is about 0.50 mm. Preferably, cathode 5 has a substantially uniform diameter $d_c$ between base 31 of the cathode tip 15 and its proximal end. However, it will be appreciated that it is possible have this diameter non-uniform along the extent of cathode 5.

Preferably, cylindrical portion 32 of plasma chamber 17 has a diameter $D_{ch}$ approximately 2-2.5 times the diameter $d_c$ of cathode 5 at base 31 of cathode tip 31. In the embodiment shown in FIG. 1*b*, the cylindrical portion 15 of plasma chamber 17 has the diameter $D_{ch}$ that is 2 times the diameter $d_c$ of cathode 5 at base 31 of cathode tip 31.

Preferably, the length of plasma chamber 17 is approximately 2-2.5 times the diameter $d_c$ of cathode 5 at the base 31 of tip 15. In the embodiment shown in FIG. 1*b*, the length $L_{ch}$ of the plasma chamber 17 approximately equals the diameter of cylindrical portion 32 of plasma chamber 17, $D_{ch}$.

In the embodiment shown in FIG. 1*b*, distal end 33 of cathode 5 is positioned at a distance from the inlet 35 of plasma channel 11. This distance is approximately equal to the diameter $d_c$ of base 31 of cathode tip 15.

In the embodiment shown in FIG. 1*b*, plasma chamber 17 is in fluid communication with plasma channel 11. Plasma channel 11 has a diameter $d_{ch}$ which is approximately 0.2-0.5 mm. In the embodiment shown in FIG. 1*b*, the diameter $d_{ch}$ of plasma channel 11 is about 0.40 mm. However, it will be appreciated that the diameter $d_{ch}$ of plasma channel 11 does not need to be uniform along the extent of the plasma channel 11 and can be non-uniform to provide different desirable properties of the plasma-generating device 1.

In some embodiments, as shown in FIG. 1*b*, plasma chamber 17 comprises a cylindrical portion 32 and a tapering transitional portion 25. In those embodiments, a transitional portion 25 essentially bridges cylindrical portion 32 of plasma chamber 17 and plasma channel 11. Transitional portion 25 of plasma chamber 17 tapers downstream, from the diameter $D_{ch}$ of cylindrical portion 32 of plasma chamber 17 to the diameter $d_{ch}$ of plasma channel 11. Transitional portion 25 can be formed in a number of alternative ways. In the embodiment shown in FIG. 1*b*, the transitional portion 25 is formed as a beveled edge. Other transitions, such as concave or convex transitions, are possible. It should be noted, however, that cylindrical portion 32 of plasma chamber 17 and plasma channel 11 can be arranged in direct contact with each other without transitional portion 25.

Plasma channel 11 is partially formed by anode 7 and intermediate electrodes 9', 9'', 9''' arranged upstream of anode 7. The length of the part of plasma channel 11 formed by the intermediate electrodes (from the inlet up to the anode) is about 4-10 times the diameter $d_{ch}$ of the plasma channel 11. In the embodiment shown in FIG. 1*a*, the length of this part of plasma channel 11 is about 2.8 mm.

The part of plasma channel 11 formed by anode 7 is approximately 3-4 times the diameter $d_{ch}$ of plasma channel 11. In the embodiment shown in FIG. 1*a*, the length of the part of plasma channel 11 formed by anode 7 is about 2 mm.

The plasma-generating device 1 can be a part of a disposable instrument. For example, an instrument may comprise plasma-generating device 1, outer shell, tubes, coupling terminals, etc. and can be sold as a disposable instrument. Alternatively, only plasma-generating device 1 can be disposable and be connected to multiple-use devices.

Other embodiments and variants are also contemplated. For example, the number and shape of the intermediate electrodes 9', 9'', 9''' can be varied according to which type of plasma-generating gas is used and the desired properties of the generated plasma.

In use, the plasma-generating gas, such as argon, is supplied to the gap formed by the outer surface of cathode 5 and the inner surface of insulator sleeve 19, through the gas supply part, as described above. The supplied plasma-generating gas is passed on through plasma chamber 17 and through plasma channel 11. The plasma-generating gas is discharged through the outlet of plasma channel 11 in anode 7. Having established the gas supply, a voltage system is switched on, which initiates an electric arc discharge process in plasma channel 11 and ignites an electric arc between cathode 5 and anode 7. Before establishing the electric arc, it is preferable to supply coolant to various elements of plasma-generating device 1 through auxiliary channels 23, as described above. Having established the electric arc, plasma is generated in plasma chamber 17. The plasma is passed on through plasma channel 11 toward the outlet thereof in anode 7. The electric arc established in plasma channel 11 heats the plasma.

A suitable operating current I for the plasma-generating device 1 according to FIGS. 1*a* and 1*b* is preferably less than 10 Amperes, preferably 4-6 Amperes. The operating voltage of the plasma-generating device 1 depends, among others, on the number of intermediate electrodes 9 and their lengths. A relatively small diameter $d_{ch}$ of the plasma channel 11 enables relatively low energy consumption and, thus, relatively low operating current I when using the plasma-generating device 1.

The center of the electric arc established between cathode 5 and anode 7, along the axis of plasma channel 11, has a prevalent temperature T. Temperature T is proportional to the quotient of discharge current I and the diameter $d_{ch}$ of plasma channel 11 according to the following equation: $T=K*I/d_{ch}$. To provide a high temperature of the plasma, for example 10,000 to 15,000° C. at the outlet of plasma channel 11 in anode 7, at a relatively low current level I, the cross-section of plasma channel 11, and thus the cross-section of the electric arc should be small, in the range of 0.2-0.5 mm. With a small cross-section of the electric arc, the electric field strength in plasma channel 11 tends to be high.

What is claimed:

1. A plasma-generating device comprising:

a. an anode at a distal end of the device, the anode having a hole therethrough;

b. a plurality of intermediate electrodes electrically insulated from each other and from the anode, each of the intermediate electrodes having a hole therethrough, wherein the holes in the intermediate electrodes and the hole in the anode form a hollow space having i. a first portion, which over a substantial length of this portion has a uniform first cross-sectional area, and ii. a second portion, which over a substantial length of this portion has a uniform second cross-sectional area that is smaller than the first cross-sectional area, the second portion being downstream of the first portion;

c. a cathode having a tapered distal portion narrowing toward a distal end of the cathode, a proximal end of the tapered portion being a base of the tapered portion, the tapered portion having a length being a distance from the base of the tapered portion to the distal end of the cathode; and d. an insulator sleeve extending along and surrounding only a portion of the cathode and having a distal end, wherein only a part of the tapered portion of the cathode projects beyond the distal end of the insulator sleeve into the first portion of the hollow space, and wherein a distal end of the cathode is located some distance away from a proximal end of the second portion of the hollow space.

2. The plasma-generating device of claim 1 further comprising an outer sleeve.

3. The plasma-generating device of claim 2, wherein the outer sleeve and the anode are parts of an integral structure.

4. The plasma-generating device of claim 1 further comprising a first insulator positioned between a pair of adjacent intermediate electrodes of the plurality of intermediate electrodes, and a second insulator positioned between a distal-most intermediate electrode of the plurality of intermediate electrodes and the anode.

5. The plasma-generating device of claim 1, wherein approximately half the length of the tapered portion of the cathode projects beyond the distal end of the insulator sleeve.

6. The plasma-generating device of claim 5, wherein a length by which the projecting tapered portion of the cathode projects beyond the distal end of the insulator sleeve is approximately equal to a largest cross-sectional diameter of the cathode at the base of the tapered portion.

7. The plasma-generating device of claim 1, wherein an outside surface of the cathode and an inside surface of the insulator sleeve form a gap.

8. The plasma-generating device of claim 7, wherein the first portion of the hollow space extends from the distal end of the insulator sleeve to the proximal end of the second portion of the hollow space.

9. The plasma-generating device of claim 7, wherein the gap is in communication with the first portion of the hollow space.

10. The plasma-generating device of claim 9, wherein the first and second portions of the hollow space are connected through a transitional third portion of the hollow space tapered toward the anode.

11. The plasma-generating device of claim 9, wherein a cross-sectional area of the gap at the base of the tapered portion of the cathode is equal to or greater than the second cross-sectional area.

12. The plasma-generating device of claim 11, wherein the length of the tapered portion of the cathode is greater than a largest cross-sectional diameter of the cathode at the base of the tapered portion.

13. The plasma-generating device of claim 12, wherein the length of the tapered portion of the cathode is greater than or equal to 1.5 times the largest cross-sectional diameter of the cathode at the base of the tapered portion.

14. The plasma-generating device of claim 10, wherein the first and third portions of the hollow space are formed by a proximal-most intermediate electrode of the plurality of intermediate electrodes.

15. The plasma-generating device of claim 14, wherein a part of the second portion of the hollow space is also formed by the proximal-most intermediate electrode.

16. The plasma-generating device of claim 15, wherein a part of the second portion of the hollow space is formed by at least two of the plurality of intermediate electrodes.

17. The plasma-generating device of claim 10, wherein a combined length of the first and third portions of the hollow space is approximately equal to the length of the tapered portion of the cathode.

18. The plasma-generating device of claim 17, wherein the combined length of the first and third portions of the hollow space is approximately equal to a largest cross-sectional diameter of the first portion of the hollow space.

19. The plasma-generating device of claim 1, wherein the tapered portion of the cathode is a cone.

20. The plasma-generating device of claim 1, wherein a first distance from the base of the tapered portion of the cathode to the distal end of the insulator sleeve is equal to or greater than a second distance from the distal end of the cathode to the proximal end of the second portion of the hollow space.

21. A plasma surgical instrument comprising the plasma-generating device of claim 1.

22. The plasma surgical instrument of claim 21 adapted for laparoscopic surgery.

23. The plasma surgical instrument of claim 22 having an outer cross-sectional width of under 10 mm.

24. The plasma surgical instrument of claim 23 having an outer cross-sectional width of under 5 mm.

25. A method of using the plasma surgical instrument of claim 21 comprising a step of discharging plasma from the distal end of the plasma surgical instrument on a biological tissue.

26. The method of claim 25 further comprising one or more steps of:

cutting, vaporizing, and coagulating the biological tissue.

27. The method of claim 25, wherein the discharged plasma is substantially free of impurities.

28. The method of claim 25, wherein the biological tissue is one of liver, spleen, heart, brain, or kidney.

* * * * *